(12) United States Patent
Chaput et al.

(10) Patent No.: US 9,469,862 B2
(45) Date of Patent: Oct. 18, 2016

(54) MODIFIED POLYMERASES FOR REPLICATION OF THREOSE NUCLEIC ACIDS

(71) Applicants: John Chaput, Phoenix, AZ (US); Matthew Dunn, Scottsdale, AZ (US)

(72) Inventors: John Chaput, Phoenix, AZ (US); Matthew Dunn, Scottsdale, AZ (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 14/820,072

(22) Filed: Aug. 6, 2015

(65) Prior Publication Data

US 2016/0097069 A1    Apr. 7, 2016

Related U.S. Application Data

(60) Provisional application No. 62/038,975, filed on Aug. 19, 2014.

(51) Int. Cl.
*C12N 9/12* (2006.01)
*C12P 19/34* (2006.01)
*C12P 7/34* (2006.01)

(52) U.S. Cl.
CPC ............. *C12P 19/34* (2013.01); *C12N 9/1241* (2013.01); *C12N 9/1252* (2013.01); *C12P 7/34* (2013.01); *C12Y 207/07007* (2013.01)

(58) Field of Classification Search
CPC ........................... C12N 9/1241; C12N 9/1252
See application file for complete search history.

(56) References Cited

U.S. PATENT DOCUMENTS

| | | | |
|---|---|---|---|
| 2006/0240439 A1* | 10/2006 | Smith | C12N 9/1252 435/6.12 |
| 2013/0130320 A1* | 5/2013 | Holliger | C12N 9/1241 435/91.3 |

OTHER PUBLICATIONS

J.K. Ichida et al. "High fidelity TNA synthesis by Therminator polymerase", Nucleic Acids Research 33(16):5219-5225. (Sep. 2005).*
Pinheiro, Vitor B., et al. "Synthetic genetic polymers capable of heredity and evolution." Science 336.6079 (Apr. 2012): 341-344.
Yu, Hanyang, Su Zhang, and John C. Chaput. "Darwinian evolution of an alternative genetic system provides support for TNA as an RNA progenitor." Nature chemistry 4.3 (Jan. 2012): 183-187.
Chaput, John C., Hanyang Yu, and Su Zhang. "The emerging world of synthetic genetics." Chemistry & biology 19.11 (Nov. 2012): 1360-1371.

* cited by examiner

*Primary Examiner* — Rebecca Prouty
(74) *Attorney, Agent, or Firm* — Quarles & Brady LLP

(57) ABSTRACT

Methods and compositions for replication of threose nucleic acids (TNAs) are described. The described methods include a method for transcribing a DNA template into a TNA, and a method for reverse transcribing a threose nucleic acid into a cDNA.

6 Claims, 6 Drawing Sheets

FIG. 1

```
                            20                              40                              60
                            |                               |                               |
9N-RI  atgattctggataccgattacattaccgaaaacggcaaaccggtgattcgtgtgttcaaa
        M  I  L  D  T  D  Y  I  T  E  N  G  K  P  V  I  R  V  F  K
                            80                             100                             120
                            |                               |                               |
9N-RI  aaagaaaacggcgaattcaaaatcgaatacgatcgtacctttgaaccgtattttacgcg
        K  E  N  G  E  F  K  I  E  Y  D  R  T  F  E  P  Y  F  Y  A
                           140                             160                             180
                            |                               |                               |
9N-RI  ctgctgaaagatgatagcgcgatcgaagatgtgaaaaaagtgaccgcgaaacgtcatggc
        L  L  K  D  D  S  A  I  E  D  V  K  K  V  T  A  K  R  H  G
                           200                             220                             240
                            |                               |                               |
9N-RI  accgtggtgaaagtgaaacgtgcggaaaaagtgcagaaaaaatttctgggccgtccgatt
        T  V  V  K  V  K  R  A  E  K  V  Q  K  K  F  L  G  R  P  I
                           260                             280                             300
                            |                               |                               |
9N-RI  gaagtgtggaaactgtatttcaaccatccgcaggatgtgccggcgattcgtgatcgtatt
        E  V  W  K  L  Y  F  N  H  P  Q  D  V  P  A  I  R  D  R  I
                           320                             340                             360
                            |                               |                               |
9N-RI  cgtgcgcatccggcggtggtggatatttatgaatatgatatcccgttcgcgaaacgttat
        R  A  H  P  A  V  V  D  I  Y  E  Y  D  I  P  F  A  K  R  Y
                           380                             400                             420
                            |                               |                               |
9N-RI  ctgattgataaaggcctgattccgatggaaggcgatgaagaactgaccatgctggccttt
        L  I  D  K  G  L  I  P  M  E  G  D  E  E  L  T  M  L  A  F
                           440                             460                             480
                            |                               |                               |
9N-RI  gcgattgcgaccctgtatcacgaaggcgaagaatttggcaccggcccgattctgatgatt
        A  I  A  T  L  Y  H  E  G  E  E  F  G  T  G  P  I  L  M  I
                           500                             520                             540
                            |                               |                               |
9N-RI  agctatgcggatggcagcgaagcgcgtgtgattacctggaaaaaaatcgatctgccgtat
        S  Y  A  D  G  S  E  A  R  V  I  T  W  K  K  I  D  L  P  Y
                           560                             580                             600
                            |                               |                               |
9N-RI  gtggatgtggtgagcaccgaaaaagaaatgatcaaacgctttctgcgtgtggtgcgtgaa
        V  D  V  V  S  T  E  K  E  M  I  K  R  F  L  R  V  V  R  E
                           620                             640                             660
                            |                               |                               |
9N-RI  aaagatccggatgtgctgattacctataacggcgataactttgatttcgcgtatctgaaa
        K  D  P  D  V  L  I  T  Y  N  G  D  N  F  D  F  A  Y  L  K
                           680                             700                             720
                            |                               |                               |
9N-RI  aaacgttgcgaagaactgggcatcaaatttaccctgggccgtgatggtagcgaaccgaaa
        K  R  C  E  E  L  G  I  K  F  T  L  G  R  D  G  S  E  P  K
                           740                             760                             780
                            |                               |                               |
9N-RI  attcagcgtatgggcgatcgttttgcggtggaagtgaaaggccgtattcatttgatctg
        I  Q  R  M  G  D  R  F  A  V  E  V  K  G  R  I  H  F  D  L
                           800                             820                             840
                            |                               |                               |
9N-RI  tatccggtgattcgccgtaccattaacctgccgacctataccctggaagcggtgtatgaa
        Y  P  V  I  R  R  T  I  N  L  P  T  Y  T  L  E  A  V  Y  E
```

FIG. 1 (continued)

```
             860                       880                       900
              |                         |                         |
9N-RI  gcggtgtttggcaaaccgaaagaaaaagtgtacgcggaagaaattgcgcaggcgtgggaa
        A  V  F  G  K  P  K  E  K  V  Y  A  E  E  I  A  Q  A  W  E
             920                       940                       960
              |                         |                         |
9N-RI  agcggcgaaggcctggaacgtgtggcgcgttatagcatggaagatgcgaaagtgacctat
        S  G  E  G  L  E  R  V  A  R  Y  S  M  E  D  A  K  V  T  Y
             980                       1,000                     1,020
              |                         |                         |
9N-RI  gaactgggccgtgaattttcccgatggaagcgcagctgtctcgtctgattggccagagc
        E  L  G  R  E  F  F  P  M  E  A  Q  L  S  R  L  I  G  Q  S
             1,040                     1,060                     1,080
              |                         |                         |
9N-RI  ctgtgggatgtgagccgtagcagcaccggcaacctggtggaatggtttctgctgcgtaaa
        L  W  D  V  S  R  S  S  T  G  N  L  V  E  W  F  L  L  R  K
             1,100                     1,120                     1,140
              |                         |                         |
9N-RI  gcgtataaacgtaacgaactggccccgaacaaaccggatgaacgtgaactggcccgtcgt
        A  Y  K  R  N  E  L  A  P  N  K  P  D  E  R  E  L  A  R  R
             1,160                     1,180                     1,200
              |                         |                         |
9N-RI  cgtggcggttatgcgggcggttatgtgaaagaaccggaacgtggcctgtgggataacatt
        R  G  G  Y  A  G  G  Y  V  K  E  P  E  R  G  L  W  D  N  I
             1,220                     1,240                     1,260
              |                         |                         |
9N-RI  gtgtatctggattttcgtagcctgtatccgagcattattatcacccataacgtgagcccg
        V  Y  L  D  F  R  S  L  Y  P  S  I  I  T  H  N  V  S  P
             1,280                     1,300                     1,320
              |                         |                         |
9N-RI  gataccctgaaccgtgaaggctgcaaagaatatgatgtggcgccggaagtgggccataaa
        D  T  L  N  R  E  G  C  K  E  Y  D  V  A  P  E  V  G  H  K
             1,340                     1,360                     1,380
              |                         |                         |
9N-RI  ttctgcaaagatttcccgggctttattccgagcctgctgggcgatctgctggaagaacgc
        F  C  K  D  F  P  G  F  I  P  S  L  L  G  D  L  L  E  E  R
             1,400                     1,420                     1,440
              |                         |                         |
9N-RI  cagaaaatcaaacgcaaaatgaaagcgaccgttgatccgctggaaaaaaaactgctggat
        Q  K  I  K  R  K  M  K  A  T  V  D  P  L  E  K  K  L  L  D
             1,460                     1,480                     1,500
              |                         |                         |
9N-RI  tatcgtcagcgccgtattaaaattctggccaacagcttctatggctattatggttatgcg
        Y  R  Q  R  R  I  K  I  L  A  N  S  F  Y  G  Y  Y  G  Y  A
             1,520                     1,540                     1,560
              |                         |                         |
9N-RI  aaagcgcgttggtattgcaaagaatgcgcggaaagcgtgaccgcgtggggccgtgaatat
        K  A  R  W  Y  C  K  E  C  A  E  S  V  T  A  W  G  R  E  Y
             1,580                     1,600                     1,620
              |                         |                         |
9N-RI  atcgaaatggtgatccgcgaactggaagaaaaattcggcttcaaagtgctgtatgcggat
        I  E  M  V  I  R  E  L  E  E  K  F  G  F  K  V  L  Y  A  D
             1,640                     1,660                     1,680
              |                         |                         |
9N-RI  accgatggcctgcatgcgaccattccgggtgcggatgcggaaaccgtgaaaaaaaaagcg
        T  D  G  L  H  A  T  I  P  G  A  D  A  E  T  V  K  K  K  A
```

FIG. 1(continued)

```
               1,700                    1,720                   1,740
                 |                        |                       |
9N-RI aaagaattcctgaaatacatcaatccgaaactgccgggcctgctggaactggaatatgaa
       K  E  F  L  K  Y  I  N  P  K  L  P  G  L  L  E  L  E  Y  E 1,760                    1,780                   1,800
                 |                        |                       |
9N-RI ggcttttatgtgcgtggcttttcgtgaccaaaaaaaaatacgcggtgatcgatgaagaa
       G  F  Y  V  R  G  F  F  V  T  K  K  K  Y  A  V  I  D  E  E 1,820                    1,840                   1,860
                 |                        |                       |
9N-RI ggcaaaattaccacccgtggcctggaaattgtgcgtcgtgattggagcgaaattgcgaaa
       G  K  I  T  T  R  G  L  E  I  V  R  R  D  W  S  E  I  A  K 1,880                    1,900                   1,920
                 |                        |                       |
9N-RI gaaacccaggcgcgtgtgctggaagcgattctgaaacatggcgatgtggaagaagcggtg
       E  T  Q  A  R  V  L  E  A  I  L  K  H  G  D  V  E  E  A  V 1,940                    1,960                   1,980
                 |                        |                       |
9N-RI cgtattgttaaagaagtgaccgaaaaactgagcaaatatgaagttccgccggaaaaactg
       R  I  V  K  E  V  T  E  K  L  S  K  Y  E  V  P  P  E  K  L 2,000                    2,020                   2,040
                 |                        |                       |
9N-RI gtgattcatattcaaattacccgtgatctgcgtgattataaagcgaccggtccgcatgtg
       V  I  H  I  Q  I  T  R  D  L  R  D  Y  K  A  T  G  P  H  V 2,060                    2,080                   2,100
                 |                        |                       |
9N-RI gcggtggcaaaacgtctggcagcgcgtggcgtgaaaattcgtccgggcaccgtgattagc
       A  V  A  K  R  L  A  A  R  G  V  K  I  R  P  G  T  V  I  S 2,120                    2,140                   2,160
                 |                        |                       |
9N-RI tatattgtgctgaaaggcagcggccgtattggcgatcgtgcgattccggcggatgaattt
       Y  I  V  L  K  G  S  G  R  I  G  D  R  A  I  P  A  D  E  F 2,180                    2,200                   2,220
                 |                        |                       |
9N-RI gatccgaccaaacatcgttatgatgcggaatattatatcgaaaaccaggtgctgccggcg
       D  P  T  K  H  R  Y  D  A  E  Y  Y  I  E  N  Q  V  L  P  A 2,240                    2,260                   2,280
                 |                        |                       |
9N-RI gtggaacgtattctgaaagcgtttggctatcgtaaagaagatctgcgctatcagaaaacc
       V  E  R  I  L  K  A  F  G  Y  R  K  E  D  L  R  Y  Q  K  T 2,300                    2,320
                 |                        |
9N-RI aaacaggtgggcctgggcgcgtggctgaaagttaaaggcaaaaaa   (SEQ ID NO:2)
       K  Q  V  G  L  G  A  W  L  K  V  K  G  K  K  (SEQ ID NO:1)
```

US 9,469,862 B2

MODIFIED POLYMERASES FOR REPLICATION OF THREOSE NUCLEIC ACIDS

CROSS-REFERENCE TO RELATED APPLICATION

This application claims the benefit of U.S. Provisional Application No. 62/038,975, filed Aug. 19, 2014, which is incorporated by reference in its entirety for all purposes.

STATEMENT AS TO RIGHTS TO INVENTIONS MADE UNDER FEDERALLY SPONSORED RESEARCH AND DEVELOPMENT

Not applicable.

BACKGROUND

The emerging field of synthetic genetics provides an exciting opportunity to explore the structural and functional properties of synthetic genetic polymers by in vitro selection. However, achieving the goal of artificial genetics requires the ability to synthesize unnatural nucleic acid substrates ("XNA"s), such as threose-nucleic acids ("TNAs"), that are not otherwise available. Limiting this process, however, is the availability of enzymes and conditions that allow for the storage and propagation of genetic information present in unnatural nucleic acid polymers such as TNAs.

Threose nucleic acid (TNA) is an unnatural genetic polymer composed of repeating units of a-L-threofuranosyl nucleic acids with 2'3'-phosphodiester linkages. In 2001, TNA was shown to form stable antiparallel Watson-crick duplexes with complementary strands of DNA and RNA, which provides a mechanism for exchanging genetic information with DNA and RNA. The structure of an all-TNA duplex, indicates that TNA is structurally similar to A-form RNA.

The discovery of TNA as an alternative genetic polymer with an RNA-like structure inspired other laboratories to begin developing the methodology needed to explore the functional properties of TNA by in vitro selection. Much of the early work in this area focused on identifying polymerases that could recognize TNA either in the template or as a nucleoside triphosphate. From these studies, we identified several DNA polymerases that could synthesize short sequences of DNA on a TNA template and other polymerases that could copy limited stretches of TNA on a DNA template. Herdewijn reported similar findings for the transcription of tTTP on a DNA template using thermophilic polymerases.

While these results show that TNA is not easily recognized by natural enzymes, subsequent screening did lead to the discovery of Therminator DNA polymerase, an engineered form of the Archeal family B replicative DNA polymerase isolated from the *Thermococcus* species 9° N. Relative to the natural enzyme, Therminator contains the mutations D141A and E143A in the exonuclease domain, as well as the mutation A485L in the finger domain. Theminator DNA polymerase was originally developed by NEB to improve the incorporation fluorescent nucleotides for Sanger sequencing. However, we found that under certain conditions, Thermiantor DNA polymerase functions can also function as an efficient DNA-dependent TNA polymerase.

Using Therminator DNA polymerase to synthesize TNA on a DNA template, Ichida and Szostak developed a DNA display strategy to generate functional TNA molecules by in vitro selection. This method establishes a genotype—phenotype link by extending a library of self-priming DNA templates with TNA, which allows each TNA sequence to become physically connected to its own DNA message. Using DNA display, we evolved a TNA aptamer with high affinity and high specificity to human thrombin. This demonstration showed that TNA can fold into tertiary structures with ligand binding activity.

In 2013, we developed a two-enzyme replication system for TNA that mimics the natural process of RNA transcription and reverse transcription. This approach was developed to expand the range of evolutionary strategies that could be used to evolve TNA aptamers and catalysts by in vitro selection. This system uses Theminator DNA polymerase to copy DNA into TNA and the Superscript II to copy TNA back into DNA. Using this strategy, TNA replication was limited to a three letter genetic alphabet due to problems associated with the incorporation of tCTP opposite G in the template. When G residues are present in the DNA template, we observe ~30% G to C transversions in the replicated DNA (DNA to TNA to DNA), suggesting that G:G mispairing occurs during TNA synthesis.

The ability to convert genetic information back and fourth between DNA and TNA has an enormous impact on biotechnology, molecular medicine, and information storage. This technology could be used to make diagnostic and therapeutic molecules that are extremely resistant to nuclease degradation. It could also be used to store information in a biologically safe medium.

BRIEF SUMMARY

Described herein are modified polymerases, nucleic acids encoding such polymerases, and the use of TNA polymerases for replicating and evolving threose nucleic acids. Specifically, we have engineered a new version of the replicative DNA polymerase 9N (9NRI) that can function in the absence of manganese ions. We used a structure-guided design strategy that involved identifying beneficial mutations from a saturation mutagenesis library that allowed for TNA synthesis in the absence of manganese ions. 9NRI contains the mutations D141A, E143A, A485R, and E664I.

9NRI can synthesize a four nucleotide alphabet (A, T, C, and G) in the absence of manganese ions. Manganese ions decrease polymerase fidelity by altering the active site of the enzyme. If the fidelity of a polymerase is too low, the message would not be copied correctly. The ability to synthesize TNA in the absence of manganese significantly improves TNA transcription fidelity.

9NRI functions with high fidelity as a DNA dependent TNA polymerase. The ability to generate four nulcoetide TNA molecules opens the possibility for in vitro selection of complex TNA molecules that are capable of performing complex functions. Additionally, since biologically relevant molecules are usually comprised of four nucleotides, the ability to generate four nucleotide TNA molecules provides potential targeting mechanism for silencing technology. Additionally, there has been much interest in the information storage capabilities of nucleic acids. Since TNA is inherently nuclease resistant, TNA has the potential to become a highly stable and long lasting medium for storing large amounts of information.

9NRI can also synthesize oligonucleotides that have a DNA-TNA mixed sequence backbone with high efficiency and high fidelity. Chimeric TNA-DNA oligonucleotides provide a convenient strategy for controlled degradation of the oligonucleotide in a biological system. This property could be useful for the development of therapeutic TNA molecules.

Accordingly, in a first aspect disclosed herein is a nucleic acid encoding a TNA polymerase comprising an amino acid sequence at least 95% identical to SEQ ID NO:1, wherein, the residue corresponding to 141 of SEQ ID NO:1 is an alanine, residue 143 is an alanine, residue 485 is an arginine, and residue 664 is an isoleucine; and wherein the encoded DNA polymerase synthesizes a TNA in the presence of a DNA template and threose nucleotides. Other mutations may be possible in the presence of manganese, but RI is the optimal enzyme when looking at just positions 485 and 664. Other enzymes have slightly improved activity as compared to wildtype, but not as good as RI.

In some embodiments the amino acid sequence of the encoded TNA polymerase is at least 98% identical to SEQ ID NO:1. In other embodiments the amino acid sequence of the encoded TNA polymerase comprises the amino acid sequence of SEQ ID NO:1. In some embodiments the amino acid sequence of the encoded TNA polymerase consists of SEQ ID NO:1.

In some embodiments the nucleotide sequence of the nucleic acid comprises SEQ ID NO:2. In other embodiments the nucleotide sequence of the nucleic acid consists of SEQ ID NO:2.

In a related aspect provided herein is a nucleic acid expression vector comprising any of the just-mentioned nucleic acids encoding a TNA polymerase. In a related aspect provided herein is a recombinant cell comprising the foregoing expression vector.

In another aspect provided herein is a purified TNA polymerase comprising an amino acid sequence at least 95% identical to SEQ ID NO:1, wherein, the residue corresponding to 141 of SEQ ID NO:1 is an alanine, residue 143 is an alanine, residue 485 is an arginine, and residue 664 is an isoleucine; and wherein the encoded DNA polymerase synthesizes a TNA in the presence of a DNA template and threose nucleotides.

In some embodiments the amino acid sequence of the purified TNA polymerase comprises an amino acid sequence at least 98% identical to SEQ ID NO:1. In other embodiments the purified TNA polymerase comprises the amino acid sequence of SEQ ID NO:1. In other embodiments the amino acid sequence of the purified TNA polymerase consists of SEQ ID NO:1.

In a related aspect provided herein is a kit comprising any of the above-described TNA polymerases and at least one threose nucleotide (e.g., tA, tT, tG, or tC). In some embodiments the at least one threose nucleotide includes tA, tT, tG, and tC.

In yet another aspect provided herein is a method for synthesizing a TNA, comprising contacting a DNA template with: (i) a TNA polymerase comprising an amino acid sequence at least 95% identical to SEQ ID NO:1, wherein, the residue corresponding to 141 of SEQ ID NO:1 is an alanine, residue 143 is an alanine, residue 485 is an arginine, and residue 664 is an isoleucine; and wherein the encoded DNA polymerase synthesizes a TNA in the presence of a DNA template and threose nucleotides; and (ii) threose nucleotides under conditions that permit TNA polymerization.

In some embodiments the amino acid sequence of the TNA polymerase utilized in the above method is at least 98% identical to SEQ ID NO:1. In other embodiments the amino acid sequence of the TNA polymerase to be used comprises the amino acid sequence of SEQ ID NO: 1. In other embodiments. In other embodiments the amino acid sequence consists of SEQ ID NO:1.

INCORPORATION BY REFERENCE

All publications, patents, and patent applications mentioned in this specification are herein incorporated by reference to the same extent as if each individual publication, patent, and patent application was specifically and individually indicated to be incorporated by reference.

BRIEF DESCRIPTION OF THE DRAWINGS

The present invention will be better understood and features, aspects and advantages other than those set forth above will become apparent when consideration is given to the following detailed description thereof. Such detailed description makes reference to the following drawings, wherein:

FIG. 1. DNA and protein sequence of 9N-RI polymerase. 9N-RI contains the following amino acid substitutions with respect to 9N: D141A, E143A, A485R, and E664I.

DETAILED DESCRIPTION

Figure 2A:
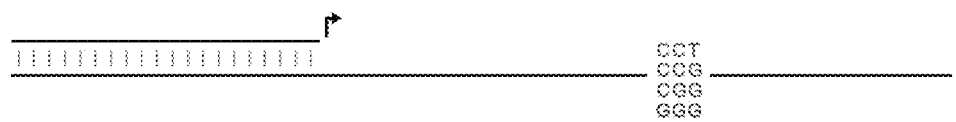
FIG. 2A. TNA transcription by 9N-RI polymerase of G series templates in the presence and absence of manganese ion. Diagram of the TNA transcription reaction depicting the four different sequences with increasing number of G nucleobases.

Disclosed herein is are methods, compositions and systems for replication and in vitro evolution of TNAs based on the unexpected finding that certain TNA synthesis conditions, as described herein, permit the efficient and faithful synthesis of XNAs from DNA templates and their reverse transcription into cDNAs using known polymerases.

Unless defined otherwise, all technical and scientific terms used herein have the same meaning as commonly understood by one of ordinary skill in the art to which the invention pertains. Although any methods and materials similar to or equivalent to those described herein can be used in the practice or testing of the present invention, the preferred methods and materials are described herein.

In describing the embodiments and claiming the invention, the following terminology will be used in accordance with the definitions set out below.

As used herein, "about" means within 5% of a stated range within the relevant parameter.

As used herein, "TNA" or "TNAs" refer to nucleic acids having a backbone composed primarily of α-L-threofuranosyl-(3'→2')(threose)-containing nucleotides, but may include heteropolymers comprising both tNTPs and dNTPs (e.g., dC).

As used herein, "TNTPs" refer to threose nucleotide triphosphates.

As used herein, "TNTP analog" refers to a threose nucleotide triphosphate having a modified base moiety.

As used herein, "TNA polymerase" refers to a polymerase capable of utilizing a DNA template and tNTPs to synthesize a complementary TNA sequence.

With respect to the amino acid sequence homology of polypeptides described herein, one of ordinary skill in the art will appreciate that structural and functional homology of two or polypeptides generally includes determining the percent identity of their amino acid sequences to each other. Sequence identity between two or more amino acid sequences is determined by conventional methods. See, for example, Altschul et al., (1997), Nucleic Acids Research, 25(17):3389-3402; and Henikoff and Henikoff (1982), Proc. Natl. Acad. Sci. USA, 89:10915 (1992). Briefly, two amino acid sequences are aligned to optimize the alignment scores using a gap opening penalty of 10, a gap extension penalty of 1, and the "BLOSUM62" scoring matrix of Henikoff and Henikoff (ibid.). The percent identity is then calculated as: ([Total number of identical matches]/[length of the longer sequence plus the number of gaps introduced into the longer sequence in order to align the two sequences])(100).

Described herein are TNA polymerases, nucleic acids encoding such TNA polymerases, and methods for synthesizing TNAs using DNA as a template. In various embodiments the TNA polymerase comprises an amino acid sequence at least 95% (e.g., 97%, 98%, 99%, or 100%) identical to the amino acid sequence of 9N-RI polymerase shown below as SEQ ID NO:1.

```
SEQ ID NO: 1; amino acid sequence of
Therminator ™ DNA polymerase.
MILDTDYITENGKPVIRVFKKENGEFKIEYDRTFEPYFYALLKDDSAIED

VKKVTAKRHGTVVKVKRAEKVQKKFLGRPIEVWKLYFNHPQDVPAIRDRI

RAHPAVVDIYEYDIPFAKRYLIDKGLIPMEGDEELTMLAFAIATLYHEGE

EFGTGPILMISYADGSEARVITWKKIDLPYVDVVSTEKEMIKRFLRVVRE

KDPDVLITYNGDNFDFAYLKKRCEELGIKFTLGRDGSEPKIQRMGDRFAV

EVKGRIHFDLYPVIRRTINLPTYTLEAVYEAVFGKPKEKVYAEEIAQAWE

SGEGLERVARYSMEDAKVTYELGREFFPMEAQLSRLIGQSLWDVSRSSTG

NLVEWFLLRKAYKRNELAPNKPDERELARRRGGYAGGYVKEPERGLWDNI

VYLDFRSLYPSIIITHNVSPDTLNREGCKEYDVAPEVGHKFCKDFPGFIP

SLLGDLLEERQKIKRKMKATVDPLEKKLLDYRQRLIKILANSFYGYYGYA

KARWYCKECAESVTAWGREYIEMVIRELEEKFGFKVLYADTDGLHATIPG

ADAETVKKKAKEFLKYINPKLPGLLELEYEGFYVRGFFVTKKKYAVIDEE

GKITTRGLEIVRRDWSEIAKETQARVLEAILKHGDVEEAVRIVKEVTEKL

SKYEVPPEKLVIHEQITRDLRDYKATGPHVAVAKRLAARGVKIRPGTVIS

YIVLKGSGRIGDRAIPADEFDPTKHRYDAEYYIENQVLPAVERILKAFGY

RKEDLRYQKTKQVGLGAWLKVKGKK.
```

In some embodiments, the DNA polymerase comprises an A485L point mutation relative to the amino acid sequence of the 9N DNA polymerase and is greater than about 95% identical to the amino acid sequence of Therminator™ DNA polymerase (Therminator™ DNA polymerase), e.g., about 96%, 97%, 98%, 99%, or 100% identical to the amino acid sequence of Therminator™ DNA polymerase. In one embodiment, the DNA polymerase to be used comprises the amino acid sequence of SEQ ID NO:1. Typically, TNA synthesis using the Therminator™ polymerase is carried out at about 50° C. to about 60° C. In some embodiments, the TNA synthesis reaction is carried out at about 55° C.

Suitable concentrations of tNTPs range from about 100 μM to about 1000 μM, e.g., about 25, 30, 35, 40, 50, 60, 70, 80, or another concentration of tNTPs from about 100 μM to about 1000 μM.

In some embodiments, the single stranded DNA template to be used in the method comprises a sequence that is restricted to the nucleotides dA, dC, and dT. While not wishing to be bound by theory, it is believed that by limiting single stranded templates to sequences containing these three nucleotides, the fidelity of the sequence transcribed into TNAs is significantly increased as described herein. Also encompassed herein are heteropolymeric TNAs generated by the above-described method, which include tA, tT, tG, and dC.

The fidelity is greatly increased in the presence of Mn if you don't have dG in the templates. These templates transcribe with high efficiency very quickly. Adding the fourth nucleotide to the react greatly reduces the fidelity in the presence of Mn while also reducing its efficiency.

Also described herein is method for reverse transcribing a TNA. In various embodiments, a TNA is reverse transcribed by a method that includes: contacting a TNA template that contains dCTP with a SuperScript II reverse transcriptase in the presence of a primer and dNTPs, and incubating the resulting mix, at a temperature suitable for SuperScript II reverse transcriptase activity, to obtain a cDNA copy of the TNA template. We can also reverse transcribe sequences containing tCTP in the TNA strand. Typically the reverse transcription reaction using the SuperScript II reverse transcriptase is carried out at a temperature of about 37° C. to about 45° C. In some embodiments, the TNA reverse transcription reaction is carried out at 42° C.

Also disclosed herein is a method for molecular evolution of threose nucleic acids, which includes the steps of: (i) providing a DNA template library containing diverse DNA template sequences; (ii) hybridizing the template library with one or more complementary primer sequences; (iii) incubating the hybridized template library with a DNA polymerase comprising an amino acid sequence at least 95% (e.g., 97%, 98%, 99%, or 100%) identical to the amino acid sequence of SEQ ID NO:1 in the presence of tTTP, tGTP, tATP, and dCTP, and incubating at a temperature suitable for polymerization by the DNA polymerase to obtain a cTNA library; (iv) subjecting the cTNA library to a selection assay to obtain at least one or more selected cTNAs; and (v) incubating the one or more selected cTNAs with a primer, a SuperScript II reverse transcriptase, and dNTPs at a temperature suitable for SuperScript II reverse transcriptase activity to obtain a selected DNA template library. In some embodiments, the diverse DNA template sequences are restricted to dA, dC, and dT, although the enzyme RI can do all four nucleotides.

TNAs can be selected from a cTNA library in step (iv) based on a number of different criteria and assays depending on a desired functionality or endpoint for the TNAs being generated. Accordingly, in some embodiments the selection assay in sep (iv) includes selection of one or more cTNAs from the cTNA library based on affinity for a ligand.

Examples of suitable affinity assays known in the art include, but are not limited to, aptamer affinity chromatography, systematic evolution of ligands by exponential enrichment (SELEX), and kinetic capillary electrophoresis. In other embodiments, selection of one or more cTNAs from the cTNA library is based on a catalytic activity. Methods for assaying and selecting catalytic activities, e.g., ribozyme activities, are known in the art as described in, e.g., Link et al. (2007), *Biol Chem* 388(8):779-786. In some embodiments, one or more cTNAs are selected based on a desired fluorescence emission. See, e.g., Paige et at (2011), *Science,* 333(6042):642-646.

In the various methods described herein, hybridization between a primer and its target sequence is generally carried out under high stringency conditions under which the primer is annealed with its complementary template sequence at a temperature approximately 5° C. below the primer's melting temperature $T_m$.

Also described herein are TNA transcription systems. In various embodiments a TNA transcription system includes the following components: a single stranded DNA template, a DNA polymerase comprising an amino acid sequence at least 95% identical to the amino acid sequence of Therminator™ DNA polymerase, tTTP, tGTP, tATP; and (i) dCTP; or (ii) a combination of tCTP and dCTP.

Also disclosed herein are TNA reverse transcription systems. Generally a TNA reverse transcription system, as described herein, includes: a TNA template comprising dC, a SuperScript II reverse transcriptase, and dNTPs.

9NRI is a more active TNA polymerase than Therminator polymerase and can be used for all of the same applications as Therminator DNA polymerase. 9NRI is better than Therminator in its ability to transcribe templates of increased complexity with higher efficiency. As a result, researchers can utilize 9NRI to generation more complex molecules with increasingly more sophisticated functions. 9NRI has potential to generate four nucleotide TNA molecules for in vitro selection of complex TNA molecules that are capable of performing complex functions. Additionally, since biologically relevant molecules are usually comprised of four nucleotides, the ability to generate four nucleotide TNA molecules provides potential targeting mechanism for silencing technology. Additionally, there has been much interest in the information storage capabilities of nucleic acids. Since TNA is inherently nuclease resistant, TNA has the potential to become a highly stable and long lasting medium for storing large amounts of information.

EXAMPLES

The invention will be more fully understood upon consideration of the following non-limiting Examples. The invention has been described in connection with what are presently considered to be the most practical and preferred embodiments. However, the present invention has been presented by way of illustration and is not intended to be limited to the disclosed embodiments. Accordingly, those skilled in the art will realize that the invention is intended to encompass all modifications and alternative arrangements within the spirit and scope of the invention as set forth in the appended claims.

Example 1

Generation of a Mutated DNA Polymerase for TNA Synthesis

In this example, we show how to prepare the mutated DNA polymerase for TNA synthesis. FIG. 1 depicts the nucleotide and amino acid sequence of 9NRI polymerase. DNA template and its corresponding primer are heated in Thermopol buffer for 5 min at 95 C. The reaction is cooled for 10 min at 4 C to promote the formation of primer-template complexes. After the 10 minute incubation, the enzyme and manganese are combined and added to the primer template complex. The reaction is then brought to 55 C. The reaction is initiated by adding tNTPs to a final concentration of 100 uM each and then incubated for the desired amount of time.

Example 2

Identification of 9NRI

Figure 2B:
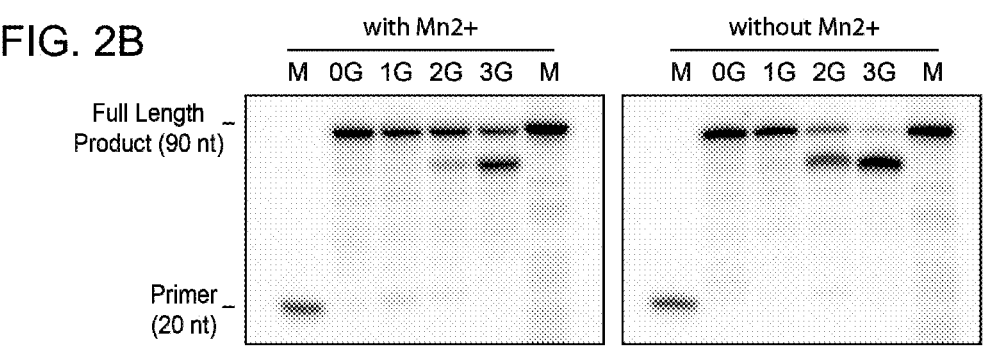
FIG. 2B. TNA transcription by 9N-RI polymerase of G series templates in the presence and absence of manganese ion. 9N-RI polymerase produces full-length TNA molecules in both the presence and absence of manganese ions. 9N-RI is the first polymerase capable of producing large quantities of TNA in the absence of manganese ions.

In this example, we describe how we identified and characterized 9NRI and its mutations D141A, E143A, A485R, and E664I. FIG. 2 depicts TNA transcription reactions of 9NRI polymerase in the presence and absence of manganese. Four different templates containing an increase number of sequential G nucleobases were combined with radiolabeled primer, tNTPs, and enzyme in the presence or absence of manganese ions. The reactions were incubated for three hours when in presence of Mn2+ and 25 hrs when in the absence of Mn2+ at 55 C. The TNA transcription reactions were analyzed by denaturing urea polyacrylamide gel electrophoresis. The gels were then imaged on a phosphorimaging screen.

Variants were generated for all 20 amino acids at positions 485 and 664 independently by site directed mutagenesis. Each variant was tested in a TNA transcription reaction and analyzed by polyacrylamide gel electrophoresis. The most active variants at positions 485 and 664 were then generated as double mutants to test for synergistic effects. The double mutants were screened in the exact method as the single mutants.

Example 3

Characterization of 9NRI

In this example, we describe the characterization of the 9NRI enzyme. 9NRI is capable of generating a significant amount of full length TNA in the absence of manganese. Previous enzymes were unable to generate any material. Additionally, 9NRI is capable of transcribing through sequences with higher numbers of sequential G nucleobases.

Example 4

Functions of 9NRI

In this example, we describe how 9NRI can synthesize a four nucleotide alphabet (A, T, C, and G) in the absence of manganese ions and why this is beneficial. 9NRI is capable of generating complex four nucleotide TNA polymers both in the presence and absence of manganese ions. Removing manganese from the transcription reactions greatly improves the fidelity of TNA transcription. The ability to generate four nucleotide TNA sequences enables the selection of biologically-relevant TNA molecules. Four nucleotide sequences have the potential to fold in more complex tertiary structures with more sophisticated functions. Additionally, since most biological genetic materials are composed of four nucleotides, four nucleotide TNA sequences can be generated to target those biomolecules. For example, nucleic acid pharmaceuticals. TNA's inherent nuclease resistance gives it even more promise for biopharmaceutical development.

Example 5

Fidelity of 9NRI

In this example, we describe how we determined that 9NRI functions with high fidelity as a DNA dependent TNA polymerase. 9NRI was discovered by screening all 20 amino acids at positions 485 and 664. Variants were expressed in XL1-blue competent cells. Clarified cell lysate was used in primer extension reactions in the presence and absence of Manganese ions. Extension efficiency was determined by comparing TNA transcription products by polyacrylamide gel electrophoresis. Single variants with the highest activity were then to look for variant combinations that synergistically improved TNA transcription.

Figure 3:
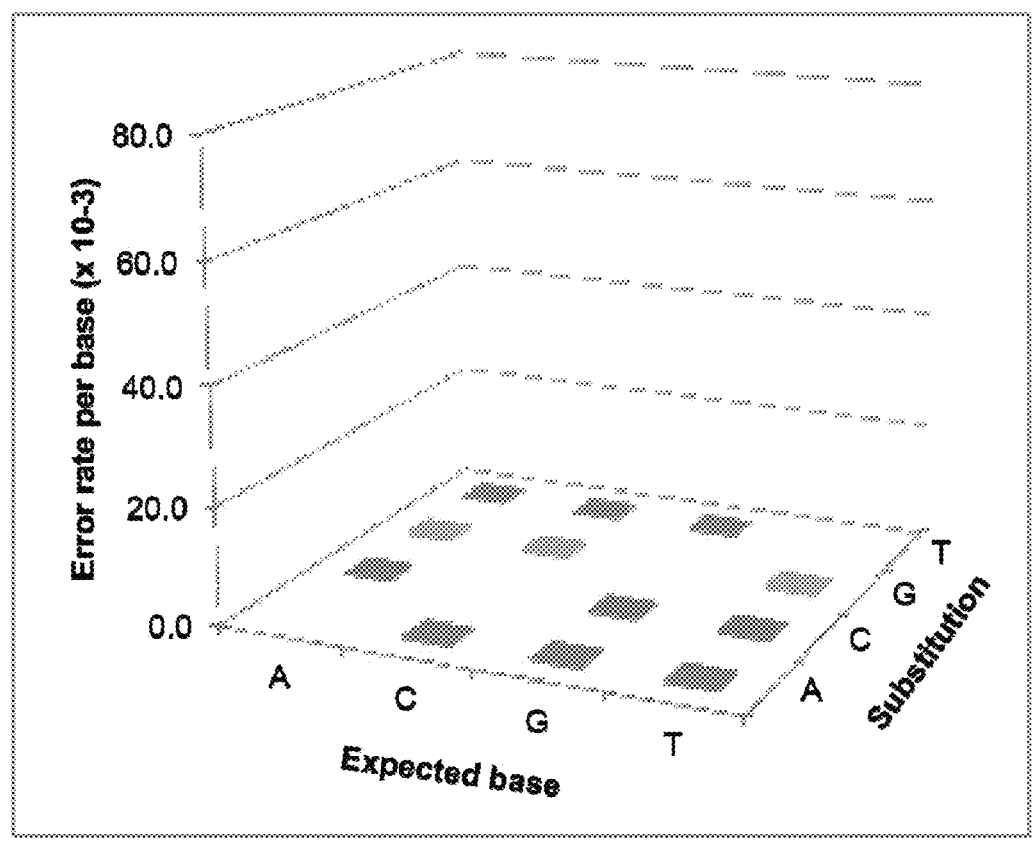
FIG. 3. Fidelity of 9N-RI in the absence of manganese. RI has a fidelity of 99.36% after sequencing 2350 nucleobases.

FIG. 3 illustrates the fidelity of TNA transcription in the absence of Mn2+. To determine the fidelity, a DNA template of a fixed sequence was transcribed into TNA using 9NRI polymerase. TNA molecules were then separated from their DNA templates by polyacrylamide gel electrophoresis, cut out of the gel, electroeluted, and then concentrated by ethanol precipitation. Purified TNA molecules were then reverse transcribed into DNA and amplified by PCR. cDNA molecules were then cloned into pJET and analyzed by DNA sequencing. The chart demonstrates that TNA transcription in the absence of Mn2+ proceeds with very high fidelity as compared to in the presence of Mn2+. Removing the Mn2+ results in approximately 12 fold reduction in the error rate of TNA transcription.

Example 6

Efficiency of 9NRI

In this example, we describe how we determined that 9NRI can synthesize oligonucleotides that have a DNA-TNA mixed sequence backbone with high efficiency and high fidelity.

Figure 4:
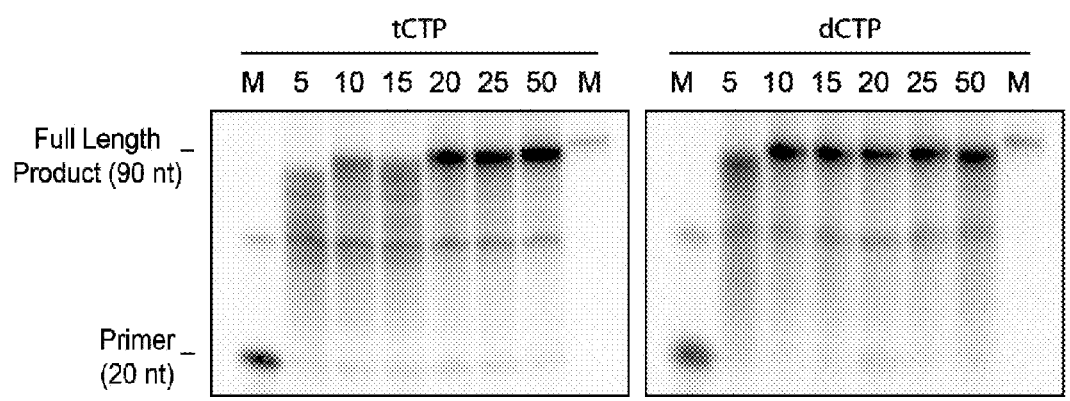
FIG. 4. 9N-RI polymerase is capable of generating pure TNA products as well as mixed TNA-DNA molecules. The gel on the left depicts the production of pure TNA molecules over time from 5 to 50 hours. The gel on the right depicts chimeric TNA-DNA molecules composed of tA, tG, tT, and dC.

FIG. 4 demonstrates the generation of mixed backbone DNA-TNA chimeric molecules. The substitution of dCTP for tCTP during TNA transcription not only allows for the generation of chimeric molecules, but it also increases the efficiency of TNA transcription. These reactions were performed as in FIG. 2 in the absence of Mn2+. Reactions were sampled every 5 hours and each sampling was analyzed by PAGE and imaged by phosphorimaging.

9NRI was tested for TNA transcription activity with both tCTP and dCTP in the TNA transcription reactions. Products were analyzed by polyacrylamide gel electrophoresis. TNA transcription was more efficient and had a higher fidelity when dCTP was present.

Example 7

Use of 9NRI

In this example, we describe how one of skill would use 9NRI. 9NRI is a highly faithful, highly efficient TNA polymerase. This polymerase enables to synthesis of complex, four-nucleotide TNA polymers. In one embodiment, these polymers can be used to generate libraries of TNA molecules for in vitro selection as well as for generating molecules capable of interacting with naturally occurring biomolecules. Other uses known to one of skill in the art can also apply.

TABLE 1

Sequences of Templates

| Name | Sequence |
| --- | --- |
| 4NT.0G (SEQ ID NO: 3) | 5'-ACTATTCAACTTACAATCCTATCAACCTTATAATCCAC TTGGCTACTGCATACGAGTGTC-3' |
| 4NT.1G (SEQ ID NO: 4) | 5'-ACTATTCAACTTACAATCGTATCAACCTTATAATCCAC TTGGCTACTGCATACGAGTGTC-3' |
| 4NT.2G (SEQ ID NO: 5) | 5'-ACTATTCAACTTACAATGGTATCAACCTTATAATCCAC TTGGCTACTGCATACGAGTGTC-3' |
| 4NT.3G (SEQ ID NO: 6) | 5'-ACTATTCAACTTACAATGGGATCAACCTTATAATCCAC TTGGCTACTGCATACGAGTGTC-3' |
| PBS2 (SEQ ID NO: 7) | 5'-GACACTCGTATGCAGTAGCC-3' |

The invention has been described in connection with what are presently considered to be the most practical and preferred embodiments. However, the present invention has been presented by way of illustration and is not intended to be limited to the disclosed embodiments. Accordingly, those skilled in the art will realize that the invention is intended to encompass all modifications and alternative arrangements within the spirit and scope of the invention as set forth in the appended claims.

We claim:

1. A purified threose nucleic acid (TNA) polymerase comprising an amino acid sequence at least 95% identical to SEQ ID NO:1, wherein, the residue corresponding to 141 of SEQ ID NO:1 is an alanine, residue 143 is an alanine, residue 485 is an arginine, and residue 664 is an isoleucine; and wherein the encoded DNA polymerase synthesizes a TNA in the presence of a DNA template and threose nucleotides.

2. The TNA polymerase of claim 1, wherein the amino acid sequence is at least 98% identical to SEQ ID NO:1.

3. A kit comprising the purified TNA polymerase of claim 1 and at least one threose nucleotide.

4. The kit of claim 3, wherein the at least one threose nucleotide comprises tA, tT, tG, and tC.

5. A method for synthesizing a TNA, comprising contacting a DNA template with:
    (i) a purified TNA polymerase comprising an amino acid sequence at least 95% identical to SEQ ID NO:1, wherein, the residue corresponding to 141 of SEQ ID NO:1 is an alanine, residue 143 is an alanine, residue 485 is an arginine, and residue 664 is an isoleucine; and wherein the encoded DNA polymerase synthesizes a TNA in the presence of a DNA template and threose nucleotides; and
    (ii) threose nucleotides under conditions that permit TNA polymerization, whereby a TNA is synthesized by the TNA polymerase.

6. The method of claim 5, wherein the amino acid sequence is at least 98% identical to SEQ ID NO:1.

* * * * *

SEQUENCE LISTING

```
<160> NUMBER OF SEQ ID NOS: 7

<210> SEQ ID NO 1
<211> LENGTH: 775
<212> TYPE: PRT
<213> ORGANISM: Thermococcus species 9N-7

<400> SEQUENCE: 1

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30
```

-continued

Thr Phe Glu Pro Tyr Phe Tyr Ala Leu Leu Lys Asp Ser Ala Ile
    35                  40                  45

Glu Asp Val Lys Lys Val Thr Ala Lys Arg His Gly Thr Val Val Lys
 50                  55                  60

Val Lys Arg Ala Glu Lys Val Gln Lys Lys Phe Leu Gly Arg Pro Ile
 65                  70                  75                  80

Glu Val Trp Lys Leu Tyr Phe Asn His Pro Gln Asp Val Pro Ala Ile
                 85                  90                  95

Arg Asp Arg Ile Arg Ala His Pro Ala Val Val Asp Ile Tyr Glu Tyr
             100                 105                 110

Asp Ile Pro Phe Ala Lys Arg Tyr Leu Ile Asp Lys Gly Leu Ile Pro
             115                 120                 125

Met Glu Gly Asp Glu Glu Leu Thr Met Leu Ala Phe Ala Ile Ala Thr
130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Arg Val Val Arg Glu Lys Asp Pro Asp Val Leu Ile Thr
        195                 200                 205

Tyr Asn Gly Asp Asn Phe Asp Phe Ala Tyr Leu Lys Lys Arg Cys Glu
            210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Gln Ala Trp Glu Ser Gly Glu Gly
290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Lys Arg Asn Glu Leu Ala
        355                 360                 365

Pro Asn Lys Pro Asp Glu Arg Glu Leu Ala Arg Arg Gly Gly Tyr
370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Leu Tyr Pro Ser Ile Ile Thr His
                405                 410                 415

Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
        435                 440                 445

Ile Pro Ser Leu Leu Gly Asp Leu Leu Glu Glu Arg Gln Lys Ile Lys

Arg Lys Met Lys Ala Thr Val Asp Pro Leu Glu Lys Lys Leu Leu Asp
465                 470                 475                 480

Tyr Arg Gln Arg Leu Ile Lys Ile Leu Ala Asn Ser Phe Tyr Gly Tyr
            485                 490                 495

Tyr Gly Tyr Ala Lys Ala Arg Trp Tyr Cys Lys Glu Cys Ala Glu Ser
        500                 505                 510

Val Thr Ala Trp Gly Arg Glu Tyr Ile Glu Met Val Ile Arg Glu Leu
    515                 520                 525

Glu Glu Lys Phe Gly Phe Lys Val Leu Tyr Ala Asp Thr Asp Gly Leu
530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Glu Glu Gly Lys Ile Thr Thr Arg Gly Leu
            595                 600                 605

Glu Ile Val Arg Arg Asp Trp Ser Glu Ile Ala Lys Glu Thr Gln Ala
610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Ala Lys Arg Leu Ala Ala
            675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
            755                 760                 765

Leu Lys Val Lys Gly Lys Lys
770                 775

<210> SEQ ID NO 2
<211> LENGTH: 2325
<212> TYPE: DNA
<213> ORGANISM: Thermococcus species 9N-7

<400> SEQUENCE: 2
atgattctgg ataccgatta cattaccgaa aacggcaaac cggtgattcg tgtgttcaaa    60
aaagaaaacg gcgaattcaa aatcgaatac gatcgtacct ttgaaccgta tttttacgcg   120
ctgctgaaag atgatagcgc gatcgaagat gtgaaaaaag tgaccgcgaa acgtcatggc   180
accgtggtga agtgaaaacg tgcggaaaaa gtgcagaaaa aatttctggg ccgtccgatt   240
gaagtgtgga aactgtattt caaccatccg caggatgtgc cggcgattcg tgatcgtatt   300

-continued

```
cgtgcgcatc cggcggtggt ggatatttat gaatatgata tcccgttcgc gaaacgttat    360
ctgattgata aaggcctgat tccgatggaa ggcgatgaag aactgaccat gctggccttt    420
gcgattgcga ccctgtatca cgaaggcgaa gaatttggca ccggcccgat tctgatgatt    480
agctatgcgg atggcagcga agcgcgtgtg attacctgga aaaaaatcga tctgccgtat    540
gtggatgtgg tgagcaccga aaagaaatg atcaaacgct ttctgcgtgt ggtgcgtgaa    600
aaagatccgg atgtgctgat tacctataac ggcgataact ttgatttcgc gtatctgaaa    660
aaacgttgcg aagaactggg catcaaattt accctgggcc gtgatggtag cgaaccgaaa    720
attcagcgta tgggcgatcg ttttgcggtg aagtgaaag gccgtattca ttttgatctg    780
tatccggtga ttcgccgtac cattaacctg ccgacctata ccctggaagc ggtgtatgaa    840
gcggtgtttg gcaaaccgaa agaaaaagtg tacgcggaag aaattgcgca ggcgtgggaa    900
agcggcgaag gcctggaacg tgtggcgcgt tatagcatgg aagatgcgaa agtgacctat    960
gaactgggcc gtgaattttt cccgatggaa gcgcagctgt ctcgtctgat ggccagagc    1020
ctgtgggatg tgagccgtag cagcaccggc aacctggtgg aatggttttct gctgcgtaaa    1080
gcgtataaac gtaacgaact ggccccgaac aaaccggatg aacgtgaact ggcccgtcgt    1140
cgtggcggtt atgcgggcgg ttatgtgaaa gaaccggaac gtggcctgtg ggataacatt    1200
gtgtatctgg attttcgtag cctgtatccg agcattatta tcacccataa cgtgagcccg    1260
gatacccctga accgtgaagg ctgcaaagaa tatgatgtgg cgccggaagt gggccataaa    1320
ttctgcaaag atttcccggg ctttattccg agcctgctgg gcgatctgct ggaagaacgc    1380
cagaaaatca acgcaaaat gaaagcgacc gttgatccgc tggaaaaaaa actgctggat    1440
tatcgtcagc gccgtattaa aattctggcc aacagcttct atggctatta tggttatgcg    1500
aaagcgcgtt ggtattgcaa agaatgcgcg gaaagcgtga ccgcgtgggg ccgtgaatat    1560
atcgaaatgg tgatccgcga actggaagaa aaattcggct tcaaagtgct gtatgcggat    1620
accgatggcc tgcatgcgac cattccgggt gcggatgcgg aaaccgtgaa aaaaaaagcg    1680
aaagaattcc tgaaatacat caatccgaaa ctgccgggcc tgctggaact ggaatatgaa    1740
ggctttatg tgcgtggctt tttcgtgacc aaaaaaaaat acgcggtgat cgatgaagaa    1800
ggcaaaatta ccacccgtgg cctggaaatt gtgcgtcgtg attggagcga aattgcgaaa    1860
gaaacccagg cgcgtgtgct ggaagcgatt ctgaacatg gcgatgtgga agaagcggtg    1920
cgtattgtta agaagtgac cgaaaaactg agcaaatatg aagttccgcc ggaaaaactg    1980
gtgattcata ttcaaattac ccgtgatctg cgtgattata agcgaccgg tccgcatgtg    2040
gcggtggcaa acgtctggc agcgcgtggc gtgaaaattc gtccgggcac cgtgattagc    2100
tatattgtgc tgaaaggcag cggccgtatt ggcgatcgtg cgattccggc ggatgaattt    2160
gatccgacca acatcgtta tgatgcggaa tattatatcg aaaaccaggt gctgccggcg    2220
gtgaacgta ttctgaaagc gtttggctat cgtaaagaag atctgcgcta tcagaaaacc    2280
aaacaggtgg gcctgggcgc gtggctgaaa gttaaaggca aaaaa          2325
```

<210> SEQ ID NO 3
<211> LENGTH: 60
<212> TYPE: DNA
<213> ORGANISM: Artificial Sequence
<220> FEATURE:
<223> OTHER INFORMATION: Sequences of Templates - 4NT.0G

<400> SEQUENCE: 3

```
actattcaac ttacaatcct atcaaccta taatccactt ggctactgca tacgagtgtc        60
```

```
<210> SEQ ID NO 4
<211> LENGTH: 60
<212> TYPE: DNA
<213> ORGANISM: Artificial Sequence
<220> FEATURE:
<223> OTHER INFORMATION: Sequences of Templates - 4NT.1G

<400> SEQUENCE: 4
actattcaac ttacaatcgt atcaaccta taatccactt ggctactgca tacgagtgtc        60
```

```
<210> SEQ ID NO 5
<211> LENGTH: 60
<212> TYPE: DNA
<213> ORGANISM: Artificial Sequence
<220> FEATURE:
<223> OTHER INFORMATION: Sequences of Templates - 4NT.2G

<400> SEQUENCE: 5
actattcaac ttacaatggt atcaaccta taatccactt ggctactgca tacgagtgtc        60
```

```
<210> SEQ ID NO 6
<211> LENGTH: 60
<212> TYPE: DNA
<213> ORGANISM: Artificial Sequence
<220> FEATURE:
<223> OTHER INFORMATION: Sequences of Templates - 4NT.3G

<400> SEQUENCE: 6
actattcaac ttacaatggg atcaaccta taatccactt ggctactgca tacgagtgtc        60
```

```
<210> SEQ ID NO 7
<211> LENGTH: 20
<212> TYPE: DNA
<213> ORGANISM: Artificial Sequence
<220> FEATURE:
<223> OTHER INFORMATION: Sequences of Templates - PBS2

<400> SEQUENCE: 7
gacactcgta tgcagtagcc                                                   20
```